United States Patent [19]

Lamprecht

[11] Patent Number: 5,875,018
[45] Date of Patent: Feb. 23, 1999

[54] PROCESS AND DEVICE FOR THE PROJECTION OF IMAGE INFORMATION FOR PERSONS WITH VISUAL IMPAIRMENT CAUSED BY DEVIATION OF THE POSITION OF THEIR OPTICAL AXIS

[76] Inventor: Jürgen Lamprecht, Pfalzgrafenstr. 24, 52072 Aachen, Germany

[21] Appl. No.: 312,108

[22] Filed: Sep. 26, 1994

[30] Foreign Application Priority Data

May 20, 1994 [DE] Germany ............................ 44 17 768.2

[51] Int. Cl.⁶ ....................................................... A61B 3/14
[52] U.S. Cl. .............................. 351/208; 351/209; 348/54
[58] Field of Search .................................... 351/210, 209, 351/211, 205, 208; 348/54

[56] References Cited

U.S. PATENT DOCUMENTS 5,422,689  6/1995  Knapp et al. ............................ 351/208

*Primary Examiner*—William L. Sikes
*Assistant Examiner*—Hung Xuan Dang
*Attorney, Agent, or Firm*—Meltzer, Lippe, Goldstein et al.

[57] ABSTRACT

A process and device for the projection of image information before at least one eye (A1,A2) of a person having a visual impairment is disclosed. The visual impairment is caused by a deviation of the angular position of the optical axis of one eye (A2) in relation to the optical axis of the other eye (A1), i.e., cross-eyed. The process and/or device enables a cross-eyed person to see stereoscopically over a long period of time without any restriction in his/her field of vision. According to the process, one eye (A1) is selected as the leading eye, the movement of the leading eye (A1) is then detected, the position of the optical axis of that eye (A1) is determined from the detected movement, and image information is projected before the non-leading eye (A2) while taking an angular deviation into account. The projected image information is identical with the image information which the non-leading eye would perceive if its optical axis was in a position corresponding to the angular position of the leading eye. The device according to the invention comprises, means (1,2) for detecting movement of at least one eye (A1) and means (3,2) for projecting an image information before the other eye (A2) while taking into account an angular deviation. The image information projected before the other eye (A2) is identical to the image information which the other eye (A2) would perceive if the position of its optical axis were to coincide with the angular position of the at least one eye (A1)

16 Claims, 1 Drawing Sheet

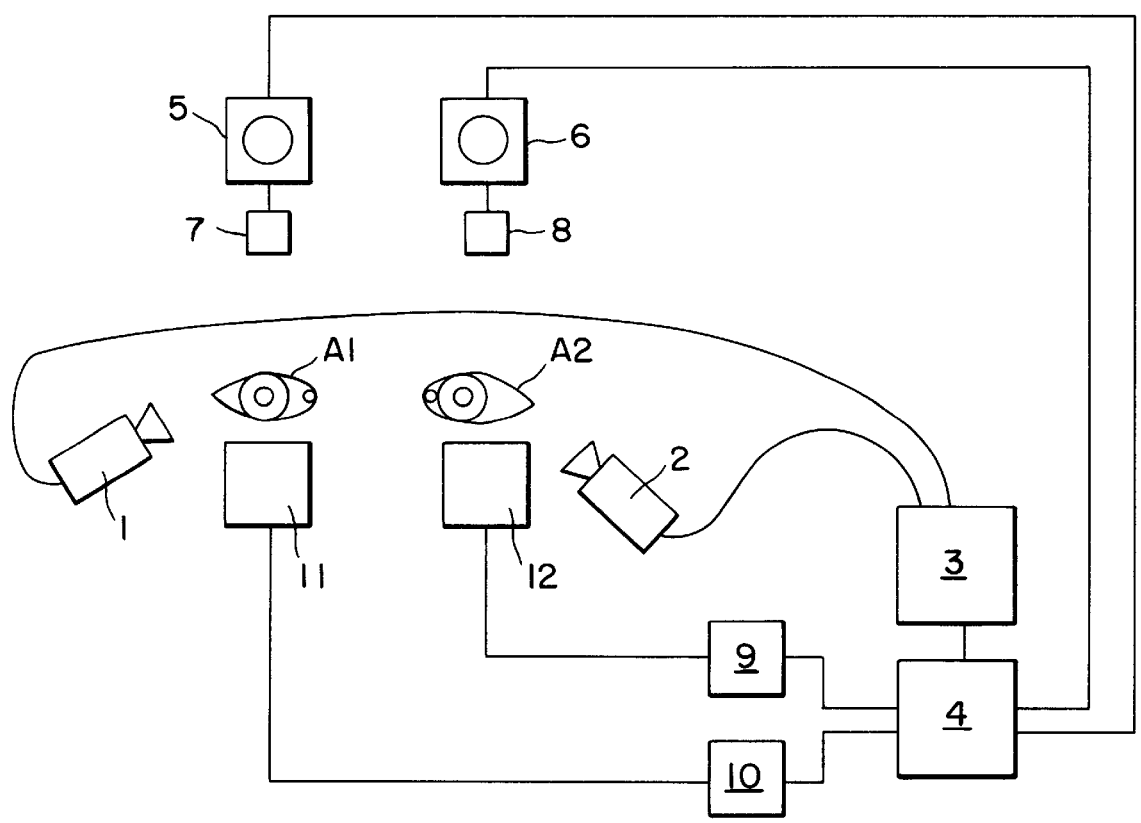

PROCESS AND DEVICE FOR THE PROJECTION OF IMAGE INFORMATION FOR PERSONS WITH VISUAL IMPAIRMENT CAUSED BY DEVIATION OF THE POSITION OF THEIR OPTICAL AXIS

FIELD OF THE INVENTION

The invention relates to a process and a device for the projection of image information before at least one eye of a person having a visual impairment. The visual impairment is caused by a deviation of the angular position of the optical axis of one eye from the optical axis of the other eye.

BACKGROUND OF THE INVENTION

Impairment of the mobility of an eye or a permanent different position of the optical axes of the pair of eyes, generally known as being cross-eyed, cause double vision because of the different image segments seen by the two eyes. The superimposition of the two different images in the brain leads to considerable disorientation in the affected person. Therefore, a competition between visual perceptions occurs in the brain of the affected person. The image which receives most of the attention dominates in the long run while the other image is suppressed. As a rule, the dominating image is the image segment which is perceived by the eye having an optical axis positioned normally.

The suppression of the image perceived by the crossing eye leads, in most cases, to vision dimness. This dimness, which is called amblyopia, expresses itself mainly with permanently cross-eyed persons in an inability to see stereoscopically and in an impairment of the faculty to separate different objects, such as letters, within the perceived image.

Especially for children, to improve the dimness of vision in one eye caused by being cross-eyed, the eye with the stronger visual capability is covered. However, this treatment is disadvantageous because the covered eye becomes highly amblyopic within a short period of time. The person treated in this manner will appear, after removing the cover, to be almost blind in the previously covered eye. This phenomenon can often be eliminated by covering the other eye. However, in the cases where correction is not carried out, dimness of vision may remain in the otherwise healthy eye. Being cross-eyed and the resulting vision dimness or dimness from the therapy affects one's ability to self-orientate because of impairment in the field of vision.

Devices to ascertain the angle of crossing are known, for example the work of Josef Lang: Strabismus, published by Hans Huber, Stuttgart, 1986. The angle of crossing is the deviation in the position of the optical axes of both eyes. For the purpose of measuring the angle of crossing prisms, and other devices, are used. These prisms and other devices can be used to determine the angular deviation by covering one or the other eye and by observing the eye reaction. However, this process is subject to the risk of faulty diagnostic results due to faulty operation.

Furthermore, another device called a synoptophore can be used for diagnostic purposes. The synoptophore device is equipped with two small pipes swivelling on an angle scale. One end of each pipe is placed before the eyes of the person to be examined while the other end is directed upon two different objects. By swivelling at least one of the pipes from a starting position representing normal vision, the objects are portrayed in front of the eyes of the examined person so that he/she finally receives the impression of a registering, or stereoscopic image. The swivelling angle of the pipe in relation to the starting position reveals the angle by which the eyes cross in the examined person.

In addition to this process, a method is known to find the crossing angle using a device called a "video eye tracker". The video eye tracker is designed for the observation and monitoring of eye movement in order to determine the smallest angle by which eyes cross. The video eye tracking system comprises an infra-red camera the image of which may be evaluated by a computer, for example.

These known devices for determining the crossing angle are suited only for one-time examination under conditions which exist only in a doctor's office.

Therefore, it has been tried to afford cross-eyed persons a stereoscopic vision by means of prism glasses. The prism assigned to the crossed eye is set to take into account the angle by which it is crossed when looking straight ahead.

SUMMARY OF THE INVENTION

It is an object of the invention to create a process and a device which enables a person affected by vision dimness due to crossed eyes to see stereoscopically for long periods of time without restrictions of his/her field of vision.

This object is attained by a process in which one of the eyes is selected as the leading eye. Only the movement of at least the leading eye is detected. The position of the optical axis of the leading eye is determined from the detected movement. Image information is projected before the other eye while taking into account an angular deviation. The projected image information is identical with the image information that would be perceived by the non-leading eye in an angular position identical with the position of the leading eye's optical axis.

According to the invention one of the eyes is selected in a first step as the leading eye. As a rule, the leading eye is the eye with the stronger vision. However, it is also possible to select the weaker eye as the leading eye. The movement of the leading eye and, thereby, the position of its optical axis, is then continuously monitored. At the same time, an image is presented to the other eye which would perceive the image if it were to look in the same image direction as the leading eye. This presentation is made while taking into account the actual angular position of the non-leading eye so that a distortion-free image is also projected on the retina of the non-leading eye. In turn, the distortion-free image makes it possible for the affected person to see stereoscopically regardless of the actual angular deviation between the optical axes of his/her eyes. Continuous monitoring of the leading eye of the affected person makes stereoscopic vision possible over a long period of time while taking into account the normal, conscious or unconscious eye movements of any human being. Stereoscopic vision over a long period of time finally leads to a strengthening of the overall perception ability of the previously weaker eye.

In the simplest case, the angular deviation taken into account in projecting the image information on the non-leading eye can be constant and identical with the angular difference between the positions of the optical axes of the eyes. However, in many cases, especially where a permanent improvement of the cross-eyed condition is to be achieved, it is advisable to render freely adjustable the angular deviation at which the image information is projected before the non-leading eye. In this manner, it is possible, to train the crossing eye by setting appropriate angular deviations so that its own visual direction is finally the same as the eye having normal vision. Such training can occur in a visual school setting. Since the angular deviation between the stronger and the weaker eye is often not constant but is different depending on the angle of vision of the normally seeing eye, the movement of both eyes should be detected and the image information should be projected while taking into account the angular deviations of the optical axis positions of both eyes caused by deviations in movement.

Regarding the inventive device, the above-mentioned object is attained by a device comprising means to detect the movement of at least a first eye, and means for the projection of an image information in front of the second eye, while taking into account an angular deviation. The image information projected before the second eye is identical with the image information which the second eye would perceive at a position of its optical axis identical with the angular position of the first eye.

The image information may be recorded, for example, by one or two cameras and projected by suitable image-producing devices and projection devices on the screens placed before the eyes of the person using the device. It is also possible to project the image information through mirror or prism systems which are able to project the image information at least on the non-leading eye while taking into account the movement of the leading eye. The natural inward crossing of eyes which occurs when an object comes nearer must also be taken into account. A suitable telemeter could be used for this purpose. In addition, each eye is to be assigned devices which correct additional vision impairments such as far-sightedness or near-sightedness In one embodiment of the invention, a process for the projection of image information before at least one eye of a visually impaired person is provided. The visually impaired person has two eyes, wherein each eye has an optical axis. The visual impairment is caused by an angular position deviation of the optical axis of one of the eyes in relation to the visual axis of another eye. One of the eyes is selected as a leading eye and the other eye is selected as a non-leading eye. Movement of the leading eye is detected. The position of the optical axis of the leading eye is determined from the detected movement. Image information is projected before the non-leading eye while taking into consideration angular deviation of the non-leading eye. The projected image information is identical with image information that would be perceived by the non-leading eye at a position of its optical axis identical with the position of the optical axis of the leading eye.

In another embodiment of the invention, the angular deviation can correspond to the angular difference between the optical axis positions of the leading and non-leading eyes. The angular deviation by which the image information is projected before the non-leading eye can be freely adjustable.

In another embodiment of the invention, movement of both eyes can be detected and image information can be projected before both eyes while taking into account the angular deviations of the optical axis position of both eyes caused by movement deviations.

In still another embodiment of the invention, image information can be projected before each eye. The image information projected before both eyes is the same as image information which the leading eye would see in free vision.

In another embodiment of the invention, a device for the projection of image information before at least one eye of a visually impaired person is provided. The person has two eyes, wherein each eye has an optical axis. The visual impairment is caused by a deviation of the angular position of the optical axis of one of the eyes relative to the optical axis of the other eye. A means for detecting movement of the at least one eye is provided. A means for projecting an image information before the other eye while taking into account an angular deviation based on the detected movement. The image information projected before the other eye is identical with the image information which the other eye would perceive in a position of its optical axis coinciding with the angular position of the at least one eye.

In another embodiment of the invention, the device can also comprise means for detecting movement of both eyes.

In yet another embodiment of the invention, the angular deviation by which the image information is projected can be equal to the angular difference between positions of the optical axes of both eyes. The angular deviation by which the image information is projected can also be adjustable.

In still another embodiment of the invention, the device may also comprise a first video camera for producing the image information projected before the other eye, an image-processing device which converts the image information produced by the first video camera into an image corresponding to the actual angular position of the optical axis of the other eye, and an image projection device which projects the converted image information on a first screen assigned to the other eye. Additionally, the device may comprise a second video camera which projects an image comprising an image section which the at least one eye perceives in free vision, and a second screen on which the second video camera projects the image having the image section.

In yet another embodiment of the invention, the means for detecting eye movements comprises a plurality of infrared CCD cameras corresponding to each eye and an evaluating device connected to the plurality of CCD cameras which ascertains the position of either eye from the image received from the corresponding CCD camera.

In still another embodiment of the invention, the device may additionally comprise a helmet in which at least the means for detecting eye movement is installed, wherein the helmet can be placed on the head of a person.

Furthermore, in another embodiment of the invention, the device may comprise at least one device for detecting a change in distance of an object viewed by the person. The device may also comprise at least one device assigned to each eye which compensates for other visual impairments.

BRIEF DESCRIPTION OF THE DRAWINGS

The sole FIGURE shows a schematic representation of the device according to the invention.

DETAILED DESCRIPTION OF THE INVENTION

Referring to the FIGURE, the device has two infra-red CCD cameras 1,2 in a helmet (not shown) which can be placed on the head of a cross-eyed person. The CCD cameras 1,2 detect the movement of the eyes A1,A2 of the cross-eyed person. The infra-red CCD cameras 1,2 are connected to an evaluation device 3 which supplies information on the angular position of the optical axes of the eyes A1,A2 to an image-producing device 4.

In addition, two cameras 5,6, which are also mounted on the helmet, are connected to the image-producing device 4. The cameras 5,6 are equipped with telemeters which detect the movements of the person towards and away from an object. Alternatively, a video recorder or a similar source of images can be connected to the image-producing device 4. By means of adjustment devices 7,8, the cameras 5,6 can be swivelled according to any change in the angle of vision of the leading eye A1 or A2.

The image-producing device 4 supplies images to the projection devices 9,10. A screen 11,12 is connected to each of the projection devices 9, 10 via light-conducting cables. Within the image-producing device 4, the angular deviation by which the image information is shown on the screen 11 or 12 can be changed by presetting turn control parameter V. The screens 11,12 are installed in the helmet before the eyes A1,A2. At the same time, each eye A1,A2 is assigned optical devices by means of which vision errors, such as short-sightedness or far-sightedness, caused by calculation errors can be corrected.

The device described above functions as follows:

Once the eye A1 having greater visual strength and normal alignment of its optical axis has been selected as the leading eye, the camera 5, assigned to this eye A1, and the camera 6, assigned to the weaker, crossing eye A2, are appropriately adjusted. Then the infrared CCD cameras 1,2 continuously detect the movements of both eyes A1,A2.

The evaluation device 3 determines the actual position of the optical axes of both eyes A1,A2 from the images of the cameras 1,2 and supplies the pertinent information to the image-producing device 4. Due to the adjusting devices 7,8, the cameras 5,6 constantly follow the movement of the leading eye A1 in a manner corresponding to the manner of eyes of a person with normal vision and normal optical axis positions.

While taking into account the information supplied by the evaluating device 3, the pre-setting turn control parameter V and the natural convergence of the eyes which occurs as the distance to an object increases or decreases, the image-producing device 4 produces an image adapted to the visual disorder of the viewer from the image of camera 6 assigned to the non-leading eye A2. This image is projected by the projection devices 9 or 10 on the screen 12 placed before the eye A2. The corresponding image of the camera assigned to eye A1 is projected in a timely fashion on the screen 11 assigned to the leading eye A1.

Finally, the above described embodiments of the present invention are intended to be illustrative only. Numerous alternative embodiments may be devised by those skilled in the art without departing from the spirit and scope of the following claims.

I claim:

1. A process for the projection of image information before at least one eye of a visually impaired person having two eyes wherein each eye has an optical axis and the visual impairment is caused by an angular position deviation of the optical axis of one of said eyes in relation to the visual axis of another eye, said process comprising,
    selecting one of said eyes as a leading eye and the other eye as a non-leading eye,
    detecting movement of said leading eye and determining position of the optical axis of said leading eye from said detected movement, and
    projecting image information before said non-leading eye while taking into consideration angular deviation of said non-leading eye, wherein said projected image information is identical with image information that would be perceived by said non-leading eye at a position of its optical axis identical with said position of said optical axis of said leading eye.

2. The process of claim 1, wherein said angular deviation corresponds to the angular difference between said optical axis positions of said leading and non-leading eyes.

3. The process of claim 1, wherein said angular deviation by which the image information is projected before the non-leading eye is freely adjustable.

4. The process of claim 1, further comprising detecting movement of both eyes and projecting image information before both eyes while taking into account the angular deviations of the optical axis position of both eyes caused by movement deviations.

5. The process of claim 1, further comprising projecting image information before each eye.

6. The process of claim 5, wherein said image information projected before both eyes is the same as image information which said leading eye would see in free vision.

7. A device for the projection of image information before at least one eye of a visually impaired person having two eyes, wherein each eye has an optical axis and said visual impairment is caused by a deviation of the angular position of the optical axis of one of said eyes relative to the optical axis of the other eye, said device comprising,
    means for detecting movement of said at least one eye, and
    means for projecting an image information before the other eye while taking into account an angular deviation, wherein the image information projected before said other eye is identical with the image information which said other eye would perceive in a position of its optical axis coinciding with the angular position of said at least one eye.

8. The device of claim 7, further comprising means for detecting movement of both eyes.

9. The device of claim 8, wherein the angular deviation by which the image information is projected is equal to the angular difference between positions of the optical axes of both eyes.

10. The device of claim 9, wherein said angular deviation by which the image information is projected is adjustable.

11. The device of claim 7, further comprising,
    a first video camera for producing said image information projected before said other eye,
    an image-processing device which converts the image information produced by said first video camera into an image corresponding to the actual angular position of the optical axis of the other eye, and
    an image projection device which projects the converted image information on a first screen assigned to said other eye.

12. The device of claim 11, further comprising,
    a second video camera which projects an image comprising an image section which said at least one eye perceives in free vision, and
    a second screen on which said second video camera projects said image having said image section.

13. The device of claim 7, wherein said means for detecting eye movements comprises a plurality of infrared CCD cameras corresponding to each eye and an evaluating device connected to said plurality of CCD cameras which ascertains the position of either eye from the image received from the corresponding CCD camera.

14. The device of claim 7, further comprising a helmet in which at least said means for detecting eye movement is installed, wherein said helmet can be placed on the head of a person.

15. The device of claim 7, further comprising at least one device for detecting a change in distance of an object viewed by the person.

16. The device of claim 7, further comprising at least one device assigned to each eye which compensates for other visual impairments.

* * * * *